United States Patent [19]

Deaton

[11] 4,228,798

[45] Oct. 21, 1980

[54] SUCTION RECEPTACLE WITH HYGROSCOPIC FILTER

[76] Inventor: David W. Deaton, 1009 Russwood, Abilene, Tex. 79601

[21] Appl. No.: 34,992

[22] Filed: May 1, 1979

[51] Int. Cl.³ .............................................. A61M 1/00
[52] U.S. Cl. .................................................... 128/276
[58] Field of Search ............. 131/10 R; 261/DIG. 65; 55/387, 97, 528, 527, 467; 128/276, 188

[56] References Cited

U.S. PATENT DOCUMENTS

| | | | |
|---|---|---|---|
| 2,261,648 | 11/1941 | Goldstein | 251/114 |
| 2,708,982 | 5/1955 | McGuff | 55/528 |
| 3,012,322 | 12/1961 | Thompson | 32/33 |
| 3,220,409 | 11/1965 | Liloia et al. | 55/527 |
| 3,719,197 | 3/1973 | Pannier et al. | 128/276 |
| 3,738,381 | 6/1973 | Holbrook | 137/199 |
| 3,768,478 | 10/1973 | Fertik | 128/276 |
| 3,809,080 | 5/1974 | Deaton | 261/DIG. 65 |
| 3,814,098 | 6/1974 | Deaton | 128/276 |
| 3,827,452 | 8/1974 | Baumgarten | 137/205 |
| 3,866,608 | 2/1975 | Reynolds et al. | 128/276 |
| 3,889,682 | 6/1975 | Denis et al. | 128/304 |
| 3,896,733 | 7/1975 | Rosenberg | 128/214 R |
| 3,965,894 | 6/1976 | Fischer | 128/194 |
| 3,965,902 | 6/1976 | Reilly et al. | 128/276 |
| 3,982,538 | 9/1976 | Sharpe | 128/276 |
| 4,004,590 | 1/1977 | Muriot | 128/276 |
| 4,013,076 | 3/1977 | Puderbaugh | 128/276 |
| 4,029,487 | 6/1977 | Brandt | 55/309 |
| 4,033,345 | 7/1977 | Sovenson et al. | 128/214 R |
| 4,036,231 | 7/1977 | Dodge et al. | 128/276 |
| 4,111,204 | 9/1978 | Hessel | 128/276 |

OTHER PUBLICATIONS

B.O.C. Medishield, Suction Control Equipment Instruction Manual, PT No. 789,429 Issue 5, Aug. 1974, Elizabeth Way, Harlow, Essex, C M 19 5 AB England.
Gomco Service and Repair Manual, Form 1176-5-M-PJ, Rotary and Thermotic Pumps, Gomco Surgical Manufacturing Corp. 828 East Ferry St., Buffalo, N.Y. 14211.
Gomco Brochure No. FA-1, Gomco Hospital Equipment for General and Post Operative Use.
The Lancet, Aug. 9, 1958, pp. 299-300 "Dissemination of Micro-Organisms by a Surgical Pump" Ranger et al. Middlesex Hospital, London England.
Vacuum and Pressure Systems, Gast Manufacturing Corp. Benton Harbor, Mich. 1976, p. 65.
"The Principles of Vacuum and Its Use in the Hospital Environment" Ohio Medical Products, Madison Wisconsin 53701, 1974 p. 7, 8 and 20.
"Acros Instruments, Inc. Advertisement," Hospitals, J.A.H.A. 2/1/79, p. 93.
Advertisement "Vac-Gard" Sorenson Research Co., Salt Lake City, Utah 3 pp.
"The Use of Suction in Clinical Medicine", Rosen et al., British Journal of Anaesthesia vol. XXXII No. 10, Oct. 1960 Great Britain, p. 502.
"The Control of Pulmonary Infections Associated with Tracheostomy", National Nosocomial Infections Study, Quarterly Report, Bureau of Epidemiology Center for Disease Control, Atlanta, Ga. Apr. 1972.
"Ideas with Air", Gast, Booklet No. 200, Gast Manufacturing Co., Benton Harbor Mich. 49022, 1973, 20 pp.
Respiratory Therapy-Safar, pp. 173-175 F. A. Davis Co., 1965.

Primary Examiner—Robert W. Michell
Assistant Examiner—J. L. Kruter
Attorney, Agent, or Firm—Richards, Harris & Medlock

[57] ABSTRACT

A medical suction system is provided for draining fluid from a patient area. The system includes a fluid collection receptacle (12) having a suction port (34) connected to a vacuum source and a fluid receiving port (30) for receiving fluid from the patient area. A hydroscopic filter (10) is mounted between the fluid collection receptacle (12) and the vacuum source for absorbing and collecting fluid entrained in the air while continuously permitting the passage of air from the interior of the fluid collection receptacle (12) through the suction port (34) to the vacuum source.

19 Claims, 6 Drawing Figures

SUCTION RECEPTACLE WITH HYGROSCOPIC FILTER

TECHNICAL FIELD

This invention relates to medical suction systems, and more particularly to a suction system using a hygroscopic filter for absorption of fluid entrained in the air within such suction systems.

BACKGROUND ART

During the course of a surgical operation on a patient, it is often necessary to remove various body fluids, including blood, from the site of the operation. Removal and collection of such body fluids is generally accomplished using a suction receptacle connected to a vacuum source to draw the fluids through a tube for deposit and collection in a fluid collection receptacle.

Typically, suction systems utilize a fluid collection receptacle and a cover which are secured together in a fluid tight fashion. Two connections are provided in the cover, one to be connected by a tube to the source of vacuum, for example, a vacuum pump or hospital vacuum outlet station. The other connection is connected through a drainage tube to the particular area of the patient requiring drainage. The vacuum pressure applied to the receptacle carries fluid through the drainage tube to a fluid inlet port in the receptacle cover.

Fluid receptacles typically utilize a float assembly or shutoff valve positioned in line with the vacuum source. The shutoff valve is operable to close the vacuum source inlet port when the fluid collected in the receptacle rises to a predetermined level. As will be subsequently described, care must be taken to prevent premature closing of the vacuum source inlet port.

It has been found that during normal operation of a fluid collection receptacle, a substantial amount of aerosol droplets and particles are created by the force of the fluid entering the receptacle. In prior collection receptacles, these aerosol particles can be entrained in the air within the system to be drawn out the vacuum port and deposited in the vacuum tubing, regulators and the vacuum source. Such aerosol particles are not only dangerous because they can carry bacteria and the like, but the particles can also cause corrosion and other damage to the vacuum regulators and the vacuum system itself.

The fluid entering suction receptacles typically has a pH level considerably different than water. Stomach acids and body fluid pH levels can range from 3.5 to 3.9, while irrigating fluid pH levels may range from 8 to 10. Additionally, chloride salts and emesis enter suction receptacles. The presence of this high pH material causes severe corrosion of vacuum regulators. Since needle valves of many such regulators are made from turned brass, the presence of this fluid has a highly corrosive effect, causing pitting of the valve and clogging which prevents the valve from shutting off. Additionally, regulator diaphragms are typically made from neoprene rubber which is affected by the salts present in fluid entering the vacuum port from suction receptacles. These salts can cause the diaphragm to lose its resiliency and crack, such that the regulator loses its ability to smoothly operate between full on and off positions. Entrained particles can also clog the inlet and outlet opening to the regulators associated with suction systems.

The collection of fluids and materials in such regulators further provides a source of nutrients for bacteria and the regulators become a breeding ground for bacteria that can be transmitted to the patient, hospital personnel and all those in the vicinity of the regulators.

Numerous previously developed suction systems have employed shutoff valves which attempt to prevent the passage of fluid while permitting gases to pass to the source of vacuum. Such prior art systems are generally categorized as being hydrophobic in that hydrophobic filters are utilized in such systems. A hydrophobic filter is one generally categorized by being nonreactive with the liquids that it filters and is composed of material having discrete small holes which prevent the passage of water therethrough. Hydrophobic filters thus filter out aerosol droplets but do not absorb the liquid. As an illustrative example, a hydrophobic filter may be viewed as a woven fine mesh of screen such that particles larger than the mesh size are filtered. In such a hydrophobic filter, water is filtered and tends to accumulate on the surface of the filter, thereby clogging the apertures in the filter and preventing the passage of air through the filter. A typical problem thus associated with hydrophobic filters utilized in suction systems is that, due to the presence of aerosol droplets within the suction system, these aerosol droplets collect on the hydrophobic filter and cause unintentional cessation of the vacuum applied to the suction receptacle such that premature shutoff occurs. Such premature vacuum cutoff can be very dangerous during an operation. Prior art filters were therefore primarily intended for use as shutoff valves in case of fluid overflow and were not intended or effective for preventing aspiration of aerosol droplets into the vacuum line.

Generally representative of previously developed suction systems which have employed hydrophobic shutoff valves are described in U.S. Pat. No. 3,719,197 issued to Pannier, Jr., et al on Mar. 6, 1973 and entitled, "Aeseptic Suction Drainage System and Valve Therefor", U.S. Pat. No. 3,738,381 issued to Holbrook on June 12, 1973 and entitled, "Inverted Fluid Collection Receptacle" and U.S. Pat. No. 4,013,076 issued to Puderbaugh, et al on Mar. 22, 1977 and entitled "Aspirator Jar". The devices described in these patents employ hydrophobic filters to exclude the passage of fluid from the vacuum line in an overflow condition. Prior suction systems have also utilized filters in the form of screens to collect large particles such as bone fragments and chips to prevent these particles from entering the vacuum line. Such a device is described in U.S. Pat. No. 3,965,902 issued to Reilly, et al on June 29, 1976 and entitled "Disposable Fluid Collection Container". The device disclosed in the Reilly patent was manufactured and sold by Respiratory Care, Inc. of Arlington Heights, Ill. under the trade name Evacupak.

Numerous other suction systems have been manufactured and sold generally categorized as utilizing hydrophobic filters including products manufactured by Sorenson Research Company of Salt Lake City, Utah under the trade name Vac-Gard, British Oxygen Company, Ltd. of Essex, England under the trade name BOC Medishield, Air Products of Allentown, Pa. manufactured under the trademark MELCO MED, Medi-Vac Corporation of Abilene, Tex. Model No. 828014 External Aerosol Trap and products manufactured by Oxequip Health Industries of Chicago, Ill. and Vernitron Medical Products, Inc. of Carlstadt, N.J. In addition, hydrophobic filters constructed from paper have been previously developed. Hydrophobic filter suction systems have thus not been satisfactory in preventing the passage of aerosol particles into vacuum regulators and the vacuum system itself during the entire operation of the suction systems, while also giving overflow protection.

Other types of filters have also been developed for medical suction environments, but none have provided the necessary filtering of fluid and particles from the vacuum line without causing premature shutoff of the vacuum system. For example, it has been proposed to provide particulate filters incorporating natural fibers such as cotton between the suction collection canister liquid level and the suction shutoff valve. Such filters are rendered useless in an overflow condition and could allow the passage of both liquid and particles into the vacuum system prior to actual shutoff. Moreover, such natural fibers require relatively large and cumbersome filter packages and cannot maintain the desired shape, thereby tending to allow substantial air leaks at the filter periphery and at other locations. Such air leakage is magnified if such natural fibers become wet, as the fibers then tend to lose shape and actually migrate, causing even greater air leaks. Such air leaks allow direct passage of liquid and particles into the vacuum systems, thereby creating the problems previously mentioned.

A need has thus arisen for a device for use in combination with a vacuum shutoff valve which prevents the passage of fluid into the vacuum line of suction systems, but which does not cause a premature actuation of the shutoff valve to stop the flow of vacuum pressure to the suction receptacle. A need has further arisen for a device which will continually maintain its filtering integrity for preventing nutrients, bacteria and chemicals from entering regulators of vacuum sources for suction receptacles during extended use of the filter. A need has further arisen for a device that is independent of a vacuum shutoff valve to function as a filter for the vacuum line to filter bacteria nutrients, solid particles, bacteria, chemicals and aerosol particles from entering the vacuum line and regulators of suction systems.

DISCLOSURE OF THE INVENTION

In accordance with the present invention, a suction system is provided including a hygroscopic filter for preventing fluid from entering the vacuum line of a suction system and for preventing premature actuation of vacuum shutoff valves.

In accordance with the present invention, a medical suction system for draining fluid from a patient area includes a fluid collection receptacle having a suction port connected to a vacuum source and a fluid receiving port for receiving fluid from the patient area. A hygroscopic filter is mounted between the fluid receiving port and the vacuum source for absorbing and collecting fluid entrained in the medical suction system while continuously permitting the passage of air from the interior of the fluid collection receptacle through the suction port to the vacuum source.

In accordance with another aspect of the present invention, a medical suction system for connection to a vacuum source for draining fluid from a patient area includes a fluid collection receptacle having a suction port for being connected to the vacuum source. The fluid collection receptacle also includes a fluid receiving port for receiving fluid from the patient area for collection within the fluid collection receptacle. A shutoff valve is mounted in association with the fluid collection receptacle and is responsive to a predetermined height of fluid within the fluid collection receptacle for closing the suction port to prevent application of vacuum pressure from the vacuum source through the suction port to the fluid collection receptacle. A hygroscopic filter is mounted between the fluid receiving port and the vacuum source for absorbing and collecting fluid entrained in the air withdrawn from the fluid collection receptacle to prevent entry of the fluid into the vacuum source while continuously permitting the passage of air from the interior of the fluid collection receptacle through the suction port to the vacuum source prior to actuation of the shutoff valve.

In accordance with yet another aspect of the present invention, a method of draining and receiving fluid from a patient source in a medical suction system is provided. The method includes supplying vacuum pressure from a vacuum source to a collection receptacle through a suction port. The fluid is received from the patient source through a fluid receiving port for collection in the collection receptacle. Fluid particles are absorbed that are entrained in the air flow from the collection receptacle to the vacuum source and these fluid particles are contained to allow the free passage of the air flow through the suction port to the vacuum source.

BRIEF DESCRIPTION OF DRAWINGS

For a more complete understanding of the present invention and for further objects and advantages thereof, reference is now made to the following Detailed Description taken in conjunction with the accompanying Drawings in which.

DETAILED DESCRIPTION

Figure 1:
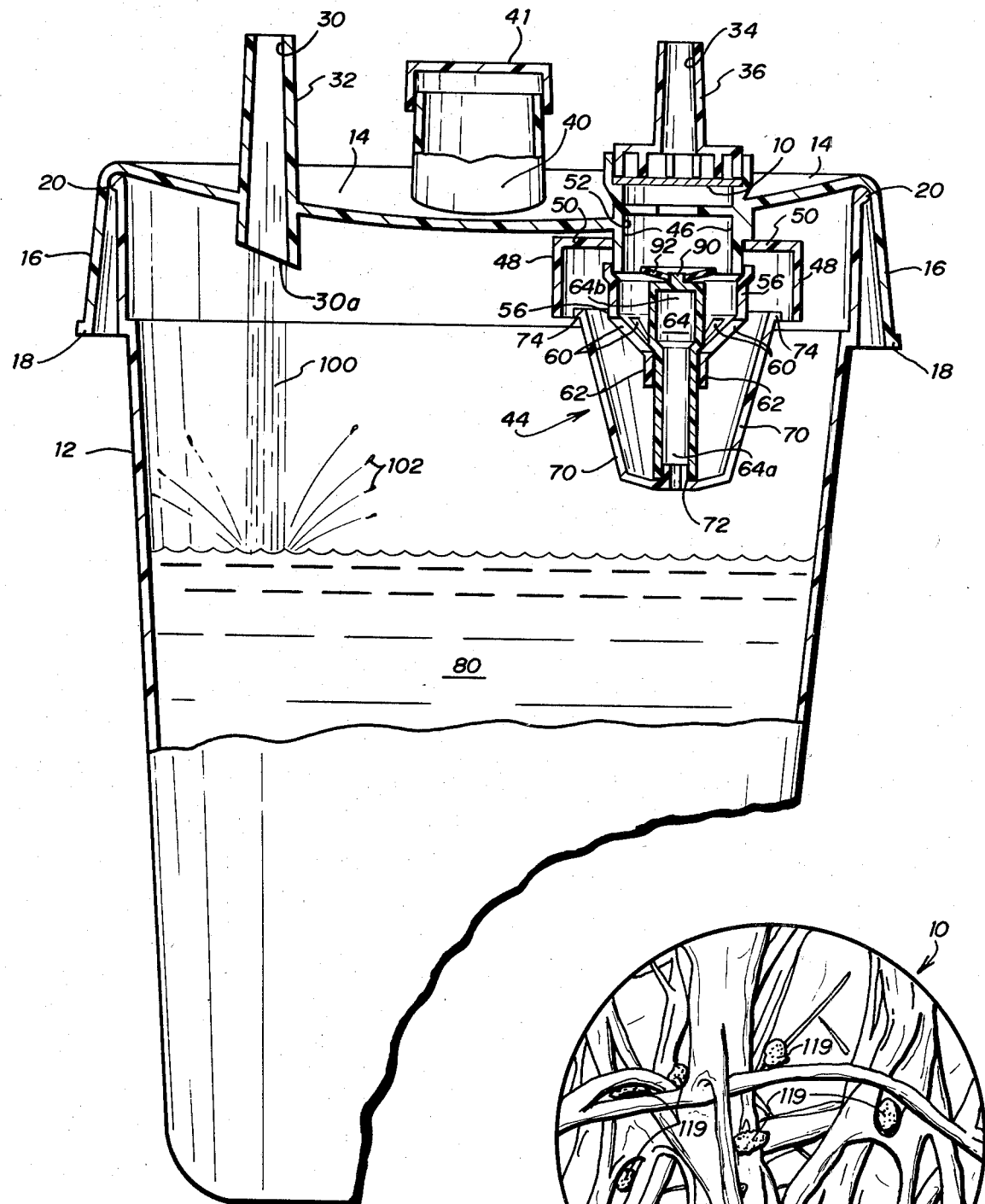
FIG. 1 is a side elevational view, partially in section, illustrating a suction receptacle utilizing the present hygroscopic filter.

Referring to FIG. 1, a suction receptacle assembly embodying the present hygroscopic filter 10 is illustrated. Hygroscopic filter 10 will be subsequently described in greater detail; however, initially it can be said that hygroscopic filter 10 is generally characterized as being water absorbent and composed of a synthetic non-woven material such as cellulose or rayon. Hygroscopic filter 10 is effective for preventing the passage of solid particles, bacteria, nutrients, bacteria and aerosol particles from passing into the vacuum source of the suction receptacle assembly.

The suction receptacle assembly includes a fluid collection receptacle 12 conventionally constructed from a suitable plastic material such as high impact styrene for receiving and collecting fluid. A cover member 14 is provided for fluid collection receptacle 12 and includes a downwardly extending annular lip 16 that is canted at a slight outward angle for providing a circumference at its lower edge 18 that is slightly greater than the circumference of fluid collection receptacle 12 at its upper edge 20. Provision of lip 16 enables cover member 14 to be easily fitted over fluid collection receptacle 12 and to be forced downwardly to form a fluid tight seal with fluid collection receptacle 12.

A fluid inlet port 30 is formed through one side of cover member 14 and includes a tapered cylinder 32 extending upwardly from cover member 14. The taper of cylinder 32 permits fluid inlet port 30 to be inserted into a flexible tubular fluid line to form a fluid tight seal. Similarly, a vacuum port 34 is provided through cover member 14 at a location spaced apart from fluid inlet port 30. Vacuum port 34 includes an upwardly extending tapered cylinder 36 for attachment to a flexible tubular vacuum line. Cover member 14 further includes a pour spout 40 for emptying fluids collected in fluid collection receptacle 12. A removable lid 41 normally covers pour spout 40.

In operation, a removable vacuum line is placed on cylinder 34 to supply vacuum pressure and to create a vacuum inside fluid collection receptacle 12. Vacuum pressure is applied through a vacuum line from a conventional hospital vacuum system or a portable vacuum supply. The vacuum created within fluid collection receptacle 12, in turn, creates a suction at the fluid inlet port 30. When a tubular fluid line is attached between cylinder 32 and a source of fluid such as a site of a surgical operation on a patient, suction at fluid inlet port 30 will withdraw fluid from the patient and cause the fluid to flow into fluid collection receptacle 12.

Associated with vacuum port 34 is a shutoff valve and protective sleeve assembly generally identified by the numeral 44. Assembly 44 includes an inner cylinder 46 integrally formed on the lower surface of cover member 14 and extending downwardly from cover member 14 in a concentric relationship with the lower end of vacuum port 34. An outer sleeve 48 depends from inner cylinder 46 utilizing a shoulder member 50 extending inwardly from the top of outer sleeve 48. Shoulder member 50 includes a centrally disposed aperture 52 for snugly fitting over inner cylinder 46. Shoulder member 50 further includes a clamping sleeve 56 which is clamped on inner cylinder 46 below shoulder member 50 for supporting shoulder member 50 and outer sleeve 48 in the position illustrated.

A plurality of spaced apart fingers 60 extend downwardly and inwardly from clamping sleeve 56. Fingers 60 support a cylindrical plunger guide 62. Plunger guide 62 is disposed in a generally vertical direction and permits a plunger 64 to be slidably mounted therein. Plunger 64 includes a cylindrical lower portion 64a that is sized to pass through and slide within plunger guide 62. Plunger 64 further includes an upper portion 64b that has a cross sectional width of sufficient area to prevent upper portion 64b from passing through plunger guide 62. It therefore can be seen that upper portion 64b of plunger 64 rests upon plunger guide 62. In this manner, plunger 64 is supported by plunger guide 62 and directed for a vertical sliding motion towards vacuum port 34.

A float 70 having a truncated conical outer configuration is removably attached to lower end 64a of plunger 64 using a prong 72. Prong 72 extends upwardly from the bottom of float 70 for insertion into lower end 64a of plunger 64 and is dimensioned to frictionally engage the interior surfaces of plunger 64 with a force sufficient to support float 70. The walls of float 70 extend upwardly such that top edge 74 of float 70 is disposed within outer sleeve 48. Outer sleeve 48 extends downwardly past top edge 74 of float 70 and partially encompasses float 70.

Shutoff valve and sleeve assembly 44 is operable to selectively block vacuum port 34 when fluid collection receptacle 12 is filled to a predetermined level with fluid. When fluid 80 contained within fluid collection receptacle 12 is below this predetermined level, float 70 and plunger 64 are supported at their lowermost position by plunger guide 62 and vacuum port 34 is in communication with the interior of fluid collection receptacle 12. When vacuum is applied to vacuum port 34, air passes from the interior of fluid collection receptacle 12 upwardly between outer sleeve 48 and top edge 74 of float 70. Air then passes downwardly along the interior walls of float 70, through the apertures between fingers 60 and then upwardly within inner cylinder 46 and through vacuum port 34. In this manner, a tortuous path is provided for the passage of air and fluid between the interior of fluid collection receptacle 12 and vacuum port 34.

When fluid 80 within fluid collection receptacle 12 reaches a predetermined level, float 70 begins to rise, causing plunger 64 to slide upwardly within plunger guide 62 towards vacuum port 34. A tab 90 extends from the top surface of plunger 64. Tab 90 functions to mount a concave flexible disc 92 mounted such that the concave surface faces vacuum port 34. The concave surface of disc 92 is dimensioned to block vacuum from vacuum port 34. As fluid 80 fills within fluid collection receptacle 12, plunger 64 is forced upwardly by float 70 until disc 92 engages vacuum port 34. In this manner, vacuum port 34 is shut off or blocked by disc 92, such that vacuum pressure is no longer applied to the interior of fluid collection receptacle 12. Therefore, fluid entering fluid collection receptacle 12 through fluid inlet port 30 will cease to flow. Further description of the illustrated float valve may be found in copending patent applications Ser. No. 923,346 entitled "Shutoff Valve Sleeve", filed July 10, 1978 and Ser. No. 923,397, entitled "Improved Shutoff Valve for Medical Suction Apparatus and Method for Making the Same", filed July 10, 1978.

An important aspect of the present invention is the provision of the hygroscopic filter 10 which is positioned in the embodiment shown in FIG. 1 above disc 92 and within inner cylinder 46 perpendicularly disposed to the path of air passing from the interior of fluid collection receptacle 12 through vacuum port 34. Alternatively, the filter may be formed in a conical shape and oriented with the apex of the cone downstream of the air flow and the base oriented upstream of the air flow. During operation of the suction system, fluid 100 enters fluid collection receptacle 12 through fluid inlet port 30. Because filter 10 is located between the shutoff valve 44 and the vacuum source, filter 10 is not affected by an overflow condition and maintains its filtering capacity up until the time the shutoff valve 44 is actuated.

Fluid 100 entering fluid collection receptacle 12 may attain velocities of about 100 miles per hour and contain a mixture of liquid and air. Because fluid 100 has been contained by the walls of inlet port 30 and the tubular fluid lines leading to inlet port 30, when fluid 100 reaches and 30a of inlet port 30 it disperses in a 360° path around inlet port end 30a. Depending upon the viscosity, internal friction, of fluid 100 and its contents, it may impact the surface of fluid 80 in a column as shown in FIG. 1. The more air within fluid 100, the wider the column becomes and the greater surface area of fluid 80 that will be impacted. If the viscosity of fluid 100 is high, there will be a narrower column of fluid within fluid collection receptacle 12 and a smaller area of impact on the surface of fluid 80.

The exiting of fluid 100 from inlet port 30 together with the impact of fluid 100 on the surface of fluid 80 creates fluid spray of heterogeneous particles of various sizes. This spray can be further classified as having splash, foam, aerosol and condensation components. An important aspect of the present invention is that hygroscopic filter 10 functions to eliminate the liquid components of fluid 100 from entering vacuum port 34. Although the splash, foam, aerosol and condensation components of fluid 100 are not specifically quantizable, it is generally agreed that splash is defined as particles having a size greater than 50 microns, illustrated as droplets 102 in FIG. 1. Foam is defined as an admixture of air and liquid, such as bubbles. Aerosol particles or droplets range from 50 microns to 0.5 microns. (See, Cushing, Ivan E. and Miller, William S. "Nebulization Theory", published in *Respiratory Therapy* edited by Peter Safar (1965 F. A. Davis Company)). Condensation is molecular water in the form of a gas.

The generated aerosol particles or droplets within fluid collection receptacle 12 propagate through collection receptacle 12 via several mechanisms. These mechanisms include movement caused by air within fluid collection receptacle 12 or aerodynamic forces, gravitational forces, temperature changes or rainout, fluid impact with mechanical baffles, subtraction of water molecules from the system and pressure changes. As a result, aerosol droplets present within fluid collection receptacle 12 are continuously changing due to the unstable environment within fluid collection receptacle 12.

As previously discussed, many prior art suction systems permitted liquid to pass from the fluid collection receptacle into the vacuum systems. Hydrophobic filtered suction systems have not absorbed the undesirable liquid, but have allowed the liquid to back up over the surface of the filter and cause unintentional blocking of vacuum. The present invention operates through the use of hygroscopic filter 10 to absorb and retain fluid particles of all sizes while allowing continuous air flow therethrough. Hence, the present invention does not result in premature shutoff of vacuum.

Generally speaking, because of its large particle size, splash can be prevented from entering the vacuum source by mechanical methods. These mechanical methods include constructing a mechanical tortuous path around the vacuum port such as that performed by shutoff valve and sleeve assembly 44. Fingers 60 (FIG. 1) effectively eliminate the splash component 102 of fluid 100 from entering vacuum port 34. Additionally, because the particle size of the splash component 102 of fluid 100 is greater than 50 microns, its velocity is slow such that mechanical baffling is effective without generating additional aerosol within fluid collection receptacle 12. Microaerosol particles do not present a substantial problem in the operation of fluid collection receptacle 12 because of their size and relatively slow speed. Microaerosol particles are primarily condensate and usually pure water, and thus do not provide serious corrosion problems. Foam particles are effectively prevented from entering vacuum port 34 because the presence of foam actuates shutoff valve 40 to close vacuum port 34. Although the control of aerosol droplets has been attempted by previously developed systems using baffles, interior pipes within fluid collection receptacles or by the design configuration of fluid collection receptacles, these methods are insufficient to completely prevent aerosol droplets from entering the vacuum port of the fluid collection receptacle. The present invention provides positive and effective aerosol particle or droplet control for suction systems.

Figure 3:
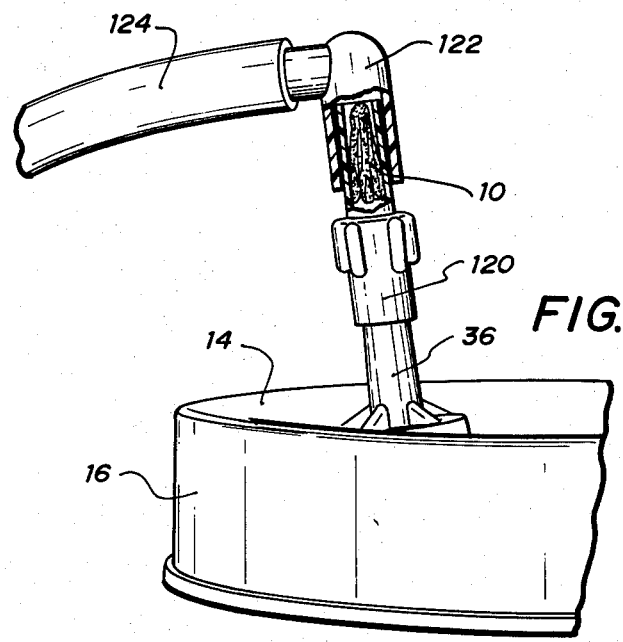
FIG. 3 is a side elevational view showing the use of the present hygroscopic filter for in-line placement between the vacuum source and vacuum port.
Figure 4:
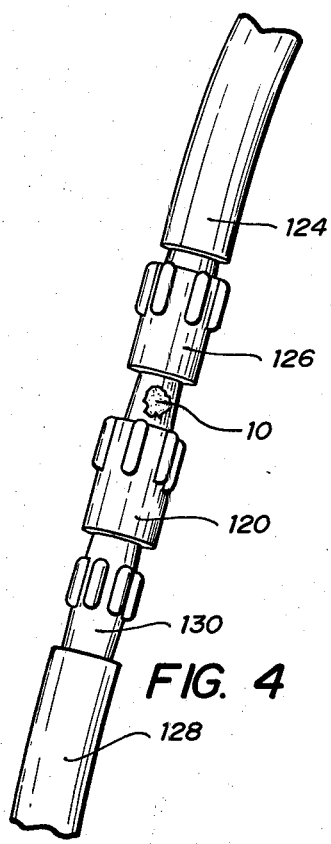
FIG. 4 illustrates the use of the present hygroscopic filter for in-line location between the vacuum source and medical suction system.

Hygroscopic filter 10 functions to absorb and retain aerosol particles or droplets within fluid collection receptacle 12 while simultaneously and continuously permitting the flow of air from the interior of fluid collection receptacle 12 to vacuum port 34. Hygroscopic filter 10, in the preferred embodiment, is die cut from sheets of filter material and has a diameter of ¾ inches and may be disposed as shown in FIG. 1, held flat, or as shown in FIGS. 3 and 4 in a cone to be subsequently described. In the preferred embodiment, the thickness of hygroscopic filter 10 ranges from a nominal 0.007 inches to a nominal 0.027 inches. The nominal weight of hygroscopic filter 10 ranges from a nominal 0.015 grams to a nominal 0.025 grams. Hygroscopic filter 10 is composed of non-woven, oriented or non-oriented fibers. Preferably, filter 10 is cut with a diameter much larger than its thickness in order to provide a large filtering surface without impeding air flow. In the preferred embodiment, hygroscopic filter 10 is composed of a synthetic non-woven rayon fiber manufactured and sold by Chicopee Manufacturing Company, Milltown, N.J. and sold under the grade number Viscon Filter Fabric No. S-850-CF-3025. Additionally, such materials as cellulose, nylon, petrochemical derivatives such as propylene and other synthetic fabric material can be treated to be hygroscopic for utilization for hygroscopic filter 10. Hygroscopic filter 10 is further characterized as being highly absorbent. Hygroscopic filter 10 in the preferred embodiment has an absorption capacity of approximately five times its weight in contradistinction to hydrophobic filters which only absorb a fraction of their weight. In accordance with the present invention, the term hygroscopic is defined as the absorption of at least 100% of the weight of the filtering substance.

Hygroscopic filter 10 functions to prevent entrained aerosol particles from entering vacuum port 34 while allowing continuous air flow through port 34. A portion of the fluid absorbed by hygroscopic filter 10 may evaporate due to the passage of air through hygroscopic filter 10 into vacuum port 34 resulting in solid particle collection on hygroscopic filter 10. The size of hygroscopic filter 10 and its absorption characteristics are chosen according to the volume of fluid to be collected by fluid collection receptacle 12.

The operation of the filter 10 has proved to be unexpectedly excellent relative to the filtering of small particulate matter such as bacteria and viruses. An important aspect of this present invention is that the filter 10 has effective pore sizes substantially greater than the dimensions of the particulate matter which is filtered from the airstream. For example, in the preferred embodiment of the invention, filter 10 is provided with an effective pore size of from approximately 15–20 microns. Yet, testing has shown that the present filter 10 filters out particulate matter having dimensions no greater than about 5 microns.

Figure 2:
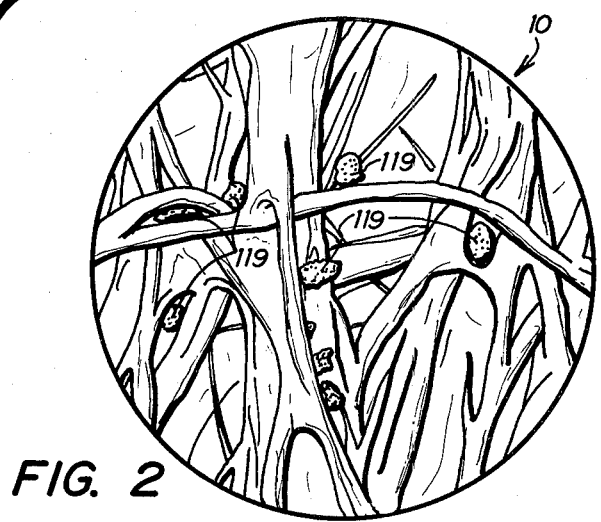
FIG. 2 is a diagrammatic representation of an electron microscopic view of the present filter showing trapped particles which have been removed from the air flow of a medical suction collection system.

The ability of the filter 10 to filter out such small particles has become understood by examination with an electron microscope. FIG. 2 illustrates a diagrammatic view of an electron microscopic picture of a portion of the present filter after use. Particles 119 are illustrated as clinging to or caught by the fibers forming the filter 10. It may be seen that the fibers of the filter 10 define effective pores having dimensions greater than the particles 119.

This phenomena may be explained by an understanding of the manner in which the majority of such particles 119 are entrained in the suction line. As previously described, a substantial amount of aerosol droplets are formed in the operation of the suction collection canister. Aerosol droplets are defined as including particulate matter such as bacteria or viruses which are covered by a layer of liquid. In some cases, more than one particle is encapsulated by liquid. Once the aerosol droplet is formed, the resulting diameter is generally substantially larger than the dimensions of the particulate matter. These aerosol droplets have dimensions thus generally equal to or greater than the dimensions of the pore sizes of the filter 10.

The aerosol droplets are then withdrawn from the airstream passing through the filter 10 and are temporarily attached to the fibers comprising the filter 10. Due to the hygroscopic nature of the filter 10, the liquid surrounding the particulate matter is absorbed by the filter 10. The absorption of the liquid covering the particulate matter then leaves the particulate matter adhering to the fibers of the filter 10 as shown in FIG. 2.

In this way, the filter 10 is able to filter out particulate matter which has dimensions substantially less than the pore size of the filter 10. This unexpected phenomena has provided the filter 10 with extremely impressive filtering capacities. It should be emphasized that the filtering of such particulate matter is accomplished by the filter 10 while also withdrawing liquid entrained in the airstream, while not impeding the flow of air therethrough. The present filter thus provides excellent protection for the medical suction system.

Substantial testing was done on the filter 10 in order to determine its filtering efficiency. These tests are set forth below:

TEST 1

To test the filter 10, an apparatus was devised to most closely duplicate hospital conditions and to determine the efficiency of the filter against a bacterial suspension. A 0.45 um filter (Falcon 7102) was used as a proven control filter to trap any bacteria which were able to penetrate the filter 10.

The apparatus consisted of:

| ITEM | PURPOSE |
|---|---|
| (1) reservoir bucket Cutter-Resiflex Enemol Enema Bucket (clean) C245, 946-10, HRI8161-0946-10 | to hold the bacterial suspension and provide a hydrostatic constant in the wound simulator |
| (2) Bacterial Suspension of: Staphylococcus aureus ATCC 25923 Pseudomonas aeruginosa ATCC 27853 Bacillus subtilis ATCC 6633 Escherichia coli ATCC 25922 | to assult filter 10 with common contaminants |
| (3) Wound simulator & Supplied by Medi-Vac, Inc. K81A Pharmaseal Lot C8J154 | to simulate the body in a 2 hour surgical operation |
| (4) Yankauer Suction Handle 6′ of ¼″ I.D. tubing Suction Collection Vessel Lot DL12785AA Supplied by Medi-Vic | to move fluids from the body (wound simulator) to the trap flask (suction collection unit) |
| (5) trap flask (suction collection unit) | to trap fluids from the body (wound simulator) by way of the Yankauer Suction Handle & tubing |
| (6) ITHAT Filter Supplied by Medi-Vac | to filter out any bacteria aerosolized by trap flask |
| (7) Falcon 7102, 0.45 micron filter with grid; Lot #80256429 | to trap any bacteria which penetrate the filter 10 |
| (8) Pump Everest & Jennings Model #H95 Lightweight Portable Aspirator SN #1466530 | to provide necessary vacuum for the system |
| (9) Tubing for all connections = Sterile Pharmaseal tubing - ¼″ I.D. | |
| (10) T-adapters, Scientific Products - 352A, Lot - #H8E145 | |

Bacterial Suspension:

Each bacteria (listed previously) was grown up on Difco Brand Brain Heart Infusion with 2% agar and harvested with sterile saline solution. The saline solutions were then mixed and diluted to an approximate volume of 6.4 liter. This suspension was then used in the test as the bacterial suspension. The bacterial suspension was placed in the enema bucket and a clamp placed on the tubing leading to the outer chamber of the wound simulator.

The apparatus was set up on a movable table in a laminar flow room. A control run consisting of the apparatus previously described with a piece of sterile Pharmaseal tubing in place of the filter unit was set up prior to each run with the filter to be tested. The filter 10 (previously sterilized by ethylene-oxide treatment) was unpacked on the laminar flow hood to insure their sterility and so as not to contaminate the others to be tested. The filter unit 10 was tested in duplicate. When tested, the filter was located between the vacuum outlet of the suction collection unit and the set of Falcon No. 7102 0.45 micron filters.

As the clamp was removed from the tubing leading to the would simulator and the pump started, a stopwatch was initiated to accurately time the procedure. At the end of one minute the pump was stopped and the clamp was placed back on the tubing. Falcon 7102's, Pharmaseal tubing, filters 10 (when in use) and T adapters were replaced with each run. The bacterial suspension was emptied from the trap flask and wound simulator between runs, and the enema bucket replenished with the bacterial suspension.

The following constants were obtained using this procedure:

maximum pressure at source=23.5 inches of Mercury
free air value=2.0 CFM
air flow through system=1.0 CFM
amount of suspension aspirated=450 ml/run After all runs were complete, Laminar flow room was scrubed with disinfectant. All non-essential equipment was autoclaved and disposed. All other equipment (i.e. pump) was cleaned with a disinfectant.

The Falcon 7102 filters were removed from their housing as aseptically transferred to plates of Difco Brand Brain Heart Infusion+2% agar and incubated for 48 hours at 32° C. These filters were counted at the end of the incubation period. Since three Falcon 7102 filter units were used for each test, the counts of the three filters should be summed. If A is the total number of organisms counted on three plates of the test in which the filter 10 was inserted, and B is the total number of organisms counted on the three plates of the control test, then:

Percent Effectiveness of the filter $10 = 100 - (A/B)100$.

Results of duplicate tests on Filter 10

| Run # | Organisms/ml with Filter | Organisms/ml without Filter | % Effectiveness |
|---|---|---|---|
| 1 | 85 | 24,288* | 99.65% |
| 2 | 111 | 18,480 | 99.40% |

Average % Effectiveness of Filter = 99.5%
*estimated

TEST 2

Materials and Apparatus:

1. Pooled bacterial suspension of:
   Staphylococcus aureus: ATCC 25923
   Pseudomonas aeruginosa: ATCC 27853
   Bacillus subtilis: ATCC 6633
   Escherichia coli: ATCC 25922
2. Fluid reservoir—plastic enema bucket.
3. Wound simulator—controlled fluid seepage device.
4. Yankauer suction handle.
5. Suction collection vessel.
6. Filters 10.
7. Membrane filtration units with 0.45 micron filters (Falcon #7102).
8. Vacuum pump, Schuco-Vac, Model #5711-130.
9. Pharmaseal plastic tubing (for all connections).
10. Tubing adapters and connectors Constants:

The following constants were maintained during the test:

| Maximum pressure at source | 21" Hg |
|---|---|
| Free air value | 1.75 CFM |
| Air flow through system | 1.0 CFM |
| Amount of bacterial suspension aspirated | 450 ml/run |

Procedure:

The test procedure is patterned after one described by Green & Vesley in *Journal of Bacteriology*, 83-3, p. 663, for the determination of the bacterial filtering efficiency of certain medical filtering materials. The procedure involves the use of a bacterial suspension of four common hospital contaminants. The suspension was made up of approximately equal concentrations of the four organisms. The organisms were propagated in pure cultures on standard methods agar. After propagation, they were harvested, pooled, washed and diluted to a convenient volume with sterile saline.

Prior to conducting the test, the filters 10, and all critical connection tubing assemblies were sterilized by ethylene oxide treatment.

In preparation for the test, the test apparatus (as described above) was set up in a certified bio-clean work area. The first test run was made without the filter 10 in place. Following this, a duplicate run was made without the filter 10, and two duplicate runs were made with the filter 10 in place.

Prior to each test run, the following sterile components were installed in the system: filters 10 (when used), membrane filtration units and all critical tubing connection assemblies.

At the start of each test run, 1000 ml of the bacterial suspension was transferred to the fluid reservoir. The tube leading from the reservoir was clamped closed during this transfer.

Next, the clamp was removed from the tube leading to the wound simulator, the vacuum pump started and a stopwatch triggered to accurately time the procedure. The bacterial suspension was allowed to flow through the system for one minute. At the end of the time period, the vacuum pump was stopped and the clamp placed back on the tube. Following each test run, the apparatus was disassembled and drained of all bacterial suspension.

After completion of all test runs, the membrane filters were aseptically transferred to standard methods agar plates. The plates were incubated 40±2 hrs. @ 35° C. After incubation, colony count determinations were made on all plates. Since three membrane filters were used for each run, the counts of all three filters were added together to indicate the total number of organisms present. No attempt was made to taxanomically identify the organisms recovered on the membranes.

The % effectiveness of the filters 10 was calculated according to the following formula:

% Filter Effectiveness = $100 - (A/B)100$ A is the total number of organisms counted on the three plates representing the test in which the filter 10 was used, and B is the total number of organisms counted on the three plates representing the control run.

Results:

Plate Count of Bacterial Suspension 280,000,000/ml

| | Bacteria Count on Membrane (with Filter 10) | Bacteria Count on Membrane (without Filter 10) | % Filter Effectiveness |
|---|---|---|---|
| Run #1 | 55 | 23,700* | 99.77% |
| Run #2 | 53 | 17,900* | 99.70% |

*Estimated Count

Conclusion:

The results of this test indicate that, when incorporated within a suction apparatus designed to simulate a surgical fluid collection system, the filter 10 effectively reduced the level of aerosolized bacterial contaminants passing through the filter by a factor or approximately 99.7%.

TEST 3

Materials:
Same as described in Test 1, except:

| Item 7 | Filter; Millipore Type HA, 0.45μ, 47mm |
|---|---|

TEST 3-continued

Materials:
Same as described in Test 1, except:

| | |
|---|---|
| | diameter, with grid, Lot No. 91511-6. |
| Item 8 | Pump; Schuco-Vac Model 5711-130, certified 1/29/79 with SCFM (free air): 1.75, static pressure: 21" Hg. |
| Item 9 | Tubing for all connections; DAVOL sterile conductive suction connecting tube, No. 3509, ¼" ID. |
| Item 10 | T-adapters; Pharmaseal plastic tubing connectors, cat. No. 356, 6 in., 1 "Y", Lot No. M5N006Y. |

Media:

Brain Heart Infusion; DIFCO, Control No. 615026.
Tryptic Soy Broth; DIFCO, Control No. 644716.
Bacto-Agar; DIFCO, Control No. 649210.

All materials were provided by Medi-Vac Corporation except Item 2, Item 7, and the bacteriological media. Materials which were to be employed as sterile materials were resterilized by Portion Packaging, Inc., South Chicago Heights, Illinois with an AMSCO spore strip control. Bacteriological media and solutions were steam pressure sterilized at 1221 C, 15 lb. pressure, for 15 min.

Sterility Checks

AMSCO spore strip, Lot No. 239BGL: No Growth.
Brain Heart Infusion plus 2% Agar: No Growth.
Tryptic Soy Broth: No Growth.

Method:

Same as Test 1, except the bacteria were suspended to a volume of 4.0 liters.

Experimental Conditions

Maximum pressure at source: 21" Hg (from pump label).
Air flow through system: 1.75 CFM (from pump label).
Volume of suspension aspirated: 425 ml.
Time of run: 1.0 min.
Total Plate Count of bacterial suspension: 400,000,000/ml.

Results:

The data presented below represent the sums of colonies developed on the three Millipore filters assembled in each run.

| Run No. | Filter 10 | Number of colonies (X) |
|---|---|---|
| 1 | Absent | 179 |
| 2 | Present | 1 |
| 3 | Absent | 257 |
| 4 Present | 0 | |

$$\text{Effectiveness} = \frac{(X_1 + S_3) - (X_2 + X_4)}{(X_1 + X_3)} \times 100\% = \frac{(179 + 257) - (1 + 0)}{(179 + 257)} \times 100\% = 99.8\%$$

Conclusion:

In comparison to the 0.45μ Millipore filter, the filter 10 is 99.8% efficient in trapping aerosol bacteria under surgical operation-simulated conditions.

Each of the above three tests were conducted by a separate independent laboratory. The results of the tests indicate that the present filter 10 provides a very high degree of filtering efficiency of small particulate matter. Additional similar tests were conducted on a large number of commercially available suction collection systems using similar tests as noted above. Suction collection systems using the filter 10 far surpassed in filter efficiency each of the other commercially available suction collection systems tested. For example, the aerosolized microorganisms which were emitted from the collection unit utilizing the present filter 10 comprised as average number of organisms per liter of collected aspirate of from 6 to 34 particles. On the contrary, the best results obtained from a competitive suction collection unit without utilizing the present filter was an average number of 8,500 organisms per liter of collected aspirate. The majority of the other suction collection units tested provided much higher numbers of aerosol micro-organisms emitted from the collection unit, up to as much as 35,500 average number of organisms per liter of collected aspirate.

The above-noted tests thus indicate that the present filter provides excellent filtering results of extremely small bacteria and the like from the airstream. Additional tests have shown that the present filter withdraws a substantial amount of liquid which is entrained in the airstream. Competitive tests of applicant's suction collection system utilizing filter 10 with commercially available suction collection systems have indicated a marked increase in liquid removed from the airstream by applicant's suction collection system.

An important aspect of the filter 10 is that the synthetic material utilized maintains its structural integrity even when wet. This resulting wet strength of the filter 10 enables the filter 10 to maintain its desired shape even though substantial amounts of liquid are absorbed. This is extremely important in that the filter 10 must be dimensioned and disposed such that no air leakage occurs around the outer edges of the filter. Such air leakage would allow direct passage of liquid and particulate matter into the suction collection system. The present system has been designed to eliminate the possibility of air leakage about the outer periphery of the filter.

The present invention thus provides superior operating characteristics to filters which use natural fibers such as cotton or the like which cannot have their parameters maintained with sufficient structural integrity to prevent leakage. Moreover, such natural fibers such as cotton tend to collapse when wet, thereby allowing additional leakage. Such problems are not present with the present filter, as it is necessary that the filter 10 has sufficient wet strength to prevent air leakage thereabout such that all air flow passes through the filter during operation.

Referring to FIG. 3, an alternative location of hygroscopic filter 10 is illustrated. Hygroscopic filter 10 is mounted external of fluid collection receptacle 12 and in line with vacuum port 34. A hollow connector 120 is engaged in fluid tight connection with vacuum port 34. Hygroscopic filter 10 is formed in a generally conical shape and is inserted within connector 120, such that the central axis of hygroscopic filter 10 is disposed substantially parallel to the direction of air flow out of fluid collection receptacle 12. The apex of the conical shape is located downstream from the flow of air. Connector 120 is interconnected in fluid tight relation to a right angle connector 122 which receives a vacuum line 124 as source of vacuum pressure. In the position as illustrated in FIG. 3, hygroscopic filter 10 functions as previously described.

Referring to FIG. 4, a further positioning of hygroscopic filter 10 is illustrated. FIG. 3 illustrates the positioning of hydrogscopic filter 10 for an in-line operation disposed between a vacuum source and fluid collection receptacle 12. Hygroscopic filter 10 is inserted into connector 120 as previously described. Connector 120 is interconnected in a fluid tight relation to a connector 126 for interconnection to vacuum line 124. Connector 120 is interconnected to a vacuum line 128 leading to fluid collection receptacle 12 using a connector 130. In the preferred embodiment, the filter 10 is formed in a conical shape and oriented with the apex downstream from the flow of air.

Figure 5:
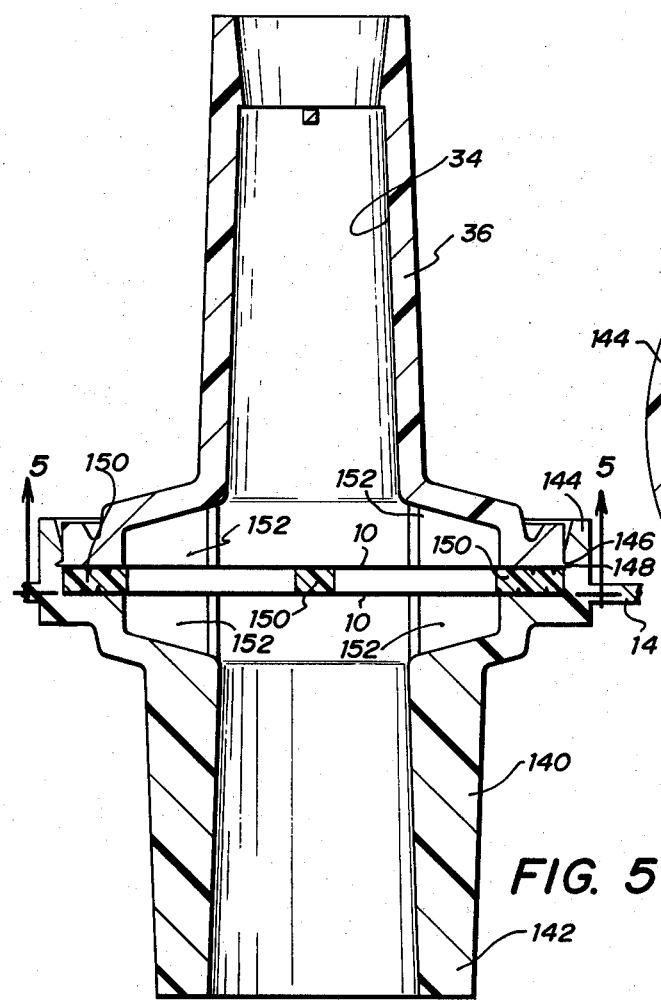
FIG. 5 is a side elevational view in section illustrating the mounting of the present hygroscopic filter in the cover of a fluid collection receptacle.
Figure 6:
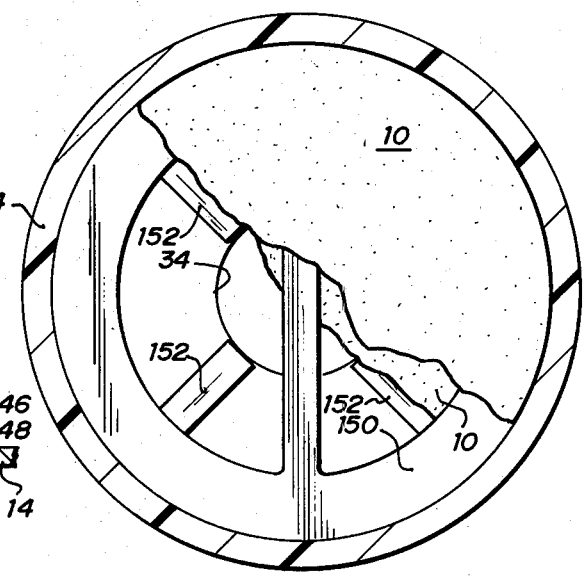
FIG. 6 is a sectional view taken generally along sectional line 5—5 of FIG. 5.

Referring simultaneously to FIGS. 5 and 6, an alternate mounting configuration of hygroscopic filter 10 is illustrated. Cover member 14 includes an integrally molded sleeve 140 having a lower portion 142 extending below cover member 14 and an upper portion 144 extending above cover member 14. Vacuum port 34 is configured for fluid tight engagement with upper portion 144 of sleeve 140, such as by using edge 146 for engagement with an undercut recess 148 within upper portion 144 of sleeve 140. Two hygroscopic filters 10 are positioned between vacuum port 34 and cover member 14 and held in position using a spacer 150 having ribs 152, more clearly illustrated in FIG. 6. In this manner, it can be seen that vacuum port 34 snaps into engagement with cover member 14 for ease in replacing hygroscopic filters 10 after use. Hygroscopic filters 10 are positioned perpendicularly to the path of air flow from the interior of fluid collection receptacle 12 and have the characteristics as previously described. Filters 10 are maintained in their desired position which extends completely across the air flow to prevent air leaks around the filter edges. The synthetic fibers of the filter 10 maintain their structural integrity even after liquid absorbtion to prevent air leakage during usage.

It therefore can be seen that the present invention prohibits aerosol droplets entrained within air contained in a fluid collection receptacle from passing into a vacuum port in a suction system. The hygroscopic filter of the present invention absorbs and collects aerosol droplets to avoid inadvertent and premature shutoff of vacuum pressure supplied to a fluid collection receptacle of a suction system.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A medical suction system for connection to a conventional hospital vacuum source having a vacuum pressure sufficient to create a suitable flow rate for draining fluid from a patient area comprising:
    a fluid collection receptacle including a suction port for being connected to the vacuum source and also including a fluid receiving port, said vacuum source creating a vacuum within said receptacle sufficient to withdraw fluid from the patient area at a desired flow rate for collection within said fluid collection receptacle;
    a shutoff valve mounted in association with said fluid collection receptacle and responsive to a predetermined height of fluid within said fluid collection receptacle for closing said suction port to prevent application of vacuum pressure from the vacuum source through said suction port to said fluid collection receptacle; and
    hygroscopic filter means for filtering aerosol droplets formed from bacteria encapsulated by liquid, said filter means mounted between said shutoff valve of said fluid collection receptacle and the vacuum source and having fibers for absorbing and collecting within the interior of said fibers liquid from said aerosol droplets entrained in the air withdrawn from said fluid collection receptacle to prevent entry of the entrained aerosol droplets into the vacuum source while continuously permitting the passage of air from the interior of said fluid collection receptacle through said suction port to the vacuum source prior to actuation of said shutoff valve, said filter having pores sized greater than the dimensions of the bacteria but generally equal to or less than the dimensions of the aerosol droplets encapsulating the bacteria in order to filter bacteria having dimensions less than about 5 microns from the air stream while allowing continuous passage of the air stream through said filter means.

2. The filter of claim 1 wherein said filter means is dimensioned to be completely disposed and maintained across the air stream to prevent leakage of air around the periphery thereof, said filter means comprising synthetic fibers having sufficient wet strength to maintain the dimensions of said filter means after absorption of liquid in order to prevent leakage of air therepast.

3. The medical suction system of claim 1 wherein said hygroscopic filter means absorbs and collects fluid aerosol particles having diameters less than approximately 50 microns.

4. The medical suction system of claim 1 wherein said hygroscopic filter means absorbs and collects bacteria having diameters greater than approximately 0.5 microns.

5. The medical suction system of claim 1 wherein said hygroscopic filter means is disposed between the fluid receiving port and the suction port.

6. The medical suction system of claim 1 wherein said hygroscopic filter means is incorporated within the suction port.

7. The medical suction system of claim 1 and further comprising: a housing mounted adjacent said suction port for housing said shutoff valve and said hygroscopic filter means.

8. The medical suction system of claim 1 wherein said hygroscopic filter means comprises a flat sheet of hygroscopic material disposed substantially perpendicular to the direction of air flow from said fluid collection receptacle.

9. The medical suction system of claim 1 wherein said hygroscopic filter means comprises a conical shaped filter member having a central axis disposed parallel to the direction of air flow from said fluid collection receptacle.

10. The medical suction system of claim 1 wherein said hygroscopic filter means comprises: first and second hygroscopic filter means spaced from one another and mounted substantially perpendicular to the flow of air from said fluid collection receptacle.

11. The medical suction system of claim 1 and further comprising a housing for said filter means, said housing being mounted for detachable engagement with said cover member for permitting replacement of said hygroscopic filter means after use.

12. The medical suction system of claim 11 and further including means for retaining said first and second hygroscopic filter means in a spaced apart relationship within said housing.

13. The filter of claim 1 wherein said filter means has a thickness between 0.007 inches and 0.027 inches in the direction of air stream flow.

14. The filter of claim 1 wherein said filter means has a liquid absorption capacity of approximately five times its weight in order to eliminate liquid from the air stream without substantially reducing the volume of the air flow.

15. A method of draining and receiving fluid from a patient source in a medical suction system while filtering aerosol droplets formed from bacteria encapsulated by liquid which are entrained in the air stream of the suction system, the system including a fluid collection receptacle having suction and fluid receiving ports, comprising the steps of:

supplying vacuum pressure from a vacuum source to the fluid collection receptacle through the suction port, said vacuum pressure being sufficient to create a suitable flow rate to draw fluid from the patient source;

receiving fluid from the patient source through the fluid receiving port for collection in the fluid collection receptacle;

disposing a filter including hygroscopic fibers in the air flow from the fluid collection receptacle to the vacuum source, said filter having pores sized greater than the dimensions of the bacterf the aerosol droplets encapsulating the bacteria in order to filter the aerosol droplets from the suction system air stream while allowing continuous passage of the air stream through said filter;

absorbing fluid from the aerosol droplets into the interior of the fibers; and containing the absorbed fluid in the fiber interiors and the bacteria on the fiber exteriors, in order to filter bacteria having dimensions less then about 5 microns from the air flow while allowing free passage of the air flow through the suction port to the vacuum source.

16. The method of claim 15 wherein aerosol droplets having diameters less than approximately 50 microns are absorbed.

17. The method of claim 15 wherein bacteria having diameters greater than approximately 0.5 microns are absorbed.

18. The method of claim 15 and further comprising: disposing first and second hygroscopic filters in spaced apart relationship to one another and substantially perpendicular to the flow of air.

19. The method of claim 15 and further comprising: disposing and maintaining said filter across the air flow to prevent leakage of air around the periphery thereof, said filter having sufficient wet strength to maintain the dimensions of said filter after absorption of liquid in order to prevent leakage of air therepast.

* * * * *

UNITED STATES PATENT AND TRADEMARK OFFICE
CERTIFICATE OF CORRECTION

PATENT NO. : 4,228,798
DATED : October 21, 1980
INVENTOR(S) : David W. Deaton

It is certified that error appears in the above—identified patent and that said Letters Patent are hereby corrected as shown below:

Column 6, line 68, change "and 30a" to --end 30a--;
Column 12, line 68, change "0.45μ" to --0.45u--;
Column 13, line 58, change "4 Present    0" to
--4        Present           0--;
Column 13, line 66, change "0.45μ" to --0.45u--;
Column 14, line 13, change "as" to -- an--;
Column 15, line 1, change "as source" to --as a source--;
Column 18, line 1, change "bacterf" to --bacteria but generally equal to or less than the dimensions of--;

Signed and Sealed this

Third Day of March 1981

[SEAL]

Attest:

RENE D. TEGTMEYER

Attesting Officer       Acting Commissioner of Patents and Trademarks